(12) United States Patent
Slattery, III et al.

(10) Patent No.: US 7,922,647 B2
(45) Date of Patent: Apr. 12, 2011

(54) SURGICAL INSTRUMENT SET AND PROCEDURE FOR IMPLANTING SOUND TRANSDUCER PROXIMATE TO PATIENT'S OUTER EAR CANAL

(75) Inventors: William H. Slattery, III, Los Angeles, CA (US); Claude A. Vidal, Santa Barbara, CA (US); Russell J. Redmond, Goleta, CA (US); Byron L. Moran, Santa Barbara, CA (US)

(73) Assignee: Advanced Bionics AG (CH)

( * ) Notice: Subject to any disclaimer, the term of this patent is extended or adjusted under 35 U.S.C. 154(b) by 1405 days.

(21) Appl. No.: 10/575,066

(22) PCT Filed: Dec. 10, 2004

(86) PCT No.: PCT/US2004/041596
§ 371 (c)(1),
(2), (4) Date: Apr. 7, 2006

(87) PCT Pub. No.: WO2005/060306
PCT Pub. Date: Jun. 30, 2005

(65) Prior Publication Data
US 2007/0028927 A1    Feb. 8, 2007

(51) Int. Cl.
*H04R 25/00* (2006.01)
(52) U.S. Cl. .......................................................... 600/25
(58) Field of Classification Search .................... 600/25; 381/312, 315, 322, 328, 329, 330, 380; 128/898; 607/55–57
See application file for complete search history.

(56) References Cited

U.S. PATENT DOCUMENTS

| | | | |
|---|---|---|---|
| 4,602,637 A | 7/1986 | Elmqvist et al. | |
| 4,645,494 A | 2/1987 | Lee et al. | |
| 4,668,222 A * | 5/1987 | Poirier | 604/175 |
| 4,774,933 A | 10/1988 | Hough et al. | |
| 4,946,444 A | 8/1990 | Heimke et al. | |
| 5,728,103 A | 3/1998 | Pincha et al. | |
| 5,772,575 A | 6/1998 | Lesinski et al. | |
| 5,814,104 A * | 9/1998 | Beoni | 623/10 |
| 5,931,838 A * | 8/1999 | Vito | 606/281 |
| 6,019,776 A | 2/2000 | Preissman et al. | |
| 6,088,619 A | 7/2000 | Hein et al. | |
| 6,094,493 A | 7/2000 | Borowsky et al. | |
| 6,293,903 B1 | 9/2001 | Kasic, II et al. | |
| 6,390,971 B1 | 5/2002 | Adams et al. | |
| 6,522,932 B1 | 2/2003 | Kuzma et al. | |
| 6,582,441 B1 | 6/2003 | He et al. | |
| 6,955,677 B2 * | 10/2005 | Dahners | 606/287 |
| 2003/0086583 A1 | 5/2003 | Maltan et al. | |

* cited by examiner

*Primary Examiner* — Samuel G Gilbert
(74) *Attorney, Agent, or Firm* — Arthur Freilich; Bryant R. Gold (57) ABSTRACT

A hearing aid system (10) including an implantable device (60), and a surgical instrument (134) for enabling a physician to install the implant (60) in a patient's body in a simple office procedure using only local anesthesia.

32 Claims, 13 Drawing Sheets

SURGICAL INSTRUMENT SET AND PROCEDURE FOR IMPLANTING SOUND TRANSDUCER PROXIMATE TO PATIENT'S OUTER EAR CANAL

FIELD OF THE INVENTION

This invention relates generally to hearing aid systems and more particularly to an implantable hearing aid device and a compatible method and surgical instrument set useful for implanting the device to project sound energy into a patient's outer ear canal.

BACKGROUND OF THE INVENTION

International application PCT/US2003/035348, which is incorporated herein by reference, describes a hearing aid system including an implant configured for placement in a recess formed between a patient's retro-auricular space and outer ear canal. The implant is described as comprising a case containing an antenna, electronic circuitry, and a transducer. The transducer functions to convert electrical signals supplied from the implant electronic circuitry into sound energy for projection into the patient's ear canal.

The hearing aid system described in said application PCT/US2003/035348 also includes a microphone module including a microphone, electronic circuitry and an antenna. Sound energy picked up by the microphone produces an output signal which is processed by the module electronic circuitry and transmitted by a telemetry link, preferably RF, to the implant. The signal received by the implant may then be further processed by the implant electronic circuitry to cause the implant transducer to project sound energy into the patient's outer ear canal.

International application PCT/US2004/011079, which is incorporated herein by reference, describes an implantable percutaneous device, and method of implantation, especially configured to promote soft tissue ingrowth for creating an infection resistant barrier and for anchoring the implanted device in place.

SUMMARY OF THE INVENTION

The present invention is directed to a hearing aid system, including an implantable device ("implant") and a surgical instrument set for enabling a physician to install the implant in a patient's body in a simple procedure, typically using only local anesthesia, while minimizing surgical time, trauma and cost. More particularly, the invention is directed to a hearing aid system including a device configured for implantation and anchoring in subcutaneous tissue adjacent to a percutaneous hole opening into a patient's ear outer canal.

In accordance with a preferred embodiment of the invention, a surgical instrument set is provided including a cannula having an elongate shaft comprised of an outer wall surrounding an elongate interior lumen. The distal end of the shaft is preferably configured with a bevel, or chisel, edge to enable the physician to tunnel the edge through subcutaneous tissue to position the edge proximate to the patient's outer ear canal. A preferred cannula embodiment in accordance with the invention carries external markings comprising a linear scale, or depth guide, viewable by the physician during the subcutaneous tunneling process. This depth guide allows the physician to accurately place the shaft distal end just short of the patient's ear canal, e.g., by 2-3 mm.

The cannula lumen has an entrance opening at its proximal end and an exit opening at its distal end to permit instruments to extend therethrough. However, in accordance with a preferred cannula embodiment, a movable door is mounted adjacent to the exit opening to prevent tissue intrusion. The door is preferably configured to be hinged closed as the cannula is advanced during the tunneling process but hinged open when pushed by an instrument passed through the cannula lumen toward the distal end.

In a preferred method of implantation in accordance with the invention, the cannula is held in place by the physician and an elongate hole forming tool is inserted through the cannula's lumen. The hole forming tool preferably comprises a handle and a shank having a cutting edge at its distal end. The preferred hole forming tool is configured so that it can be axially rotated in the cannula to axially advance the cutting edge to cut a percutaneous hole opening into the patients ear canal. Alternatively, the hole can be punched. Regardless, it is preferable the cutting edge work against an anvil, or cutting board, surface temporarily placed into the patient's ear canal to form a clean hole.

Also in accordance with a preferred method of implantation, the implant is transported through the cannula lumen to the exit opening for anchoring in subcutaneous tissue proximate to the patient's ear canal. The implant preferably comprises a housing, or case, having a peripheral surface area carrying a porous layer, e.g., titanium mesh, configured to promote tissue ingrowth for anchoring the implant.

A cannula in accordance with a preferred embodiment of the invention comprises an elongate shaft having an outer wall of noncircular, e.g., oval, cross section. This noncircular cross-section facilitates tapering the cannula shaft distal end to form a flat bevel, or chisel, edge useful for separating skin from bone as the shaft distal end is manually advanced by the physician from a retro-auricular incision to a position proximate to the patient's ear canal.

The cannula noncircular outer wall also facilitates the formation of a noncircular interior lumen. The implant housing preferably has a similar noncircular cross-section which allows it to translate along the cannula lumen toward the exit opening without rotating.

The implant housing preferably comprises a body having a laterally oriented shoulder and a distally projecting stud for extending percutaneously through the hole opening into the ear canal. Exterior surface areas of the shoulder and/or stud and/or body preferably carry porous material for encouraging soft tissue ingrowth to assist in anchoring the housing.

A preferred cannula in accordance with the invention includes a spring loaded latch carrying an index tooth engageable with various instruments insertable through the cannula lumen. A preferred instrument set in accordance with the invention includes an obturator for blocking the distal end of the cannula lumen when the cannula is being tunneled through tissue. The cannula index tooth preferably engages a mating groove in the obturator to releasably fix the obturator to the cannula.

The preferred instrument set also includes a dilator, insertable through the cannula lumen, for pushing tissue away from the lumen exit opening in preparation for using the aforementioned hole forming tool.

The preferred hole forming tool (or "hole former") includes a handle and a hollow shank having a cutting edge at its distal end. A helical groove, or thread, in the tool handle is configured to receive the cannula index tooth to initially locate the cutting edge at a starting position adjacent to the tissue surrounding the patient's ear canal. The physician is then able to axially rotate the handle to axially advance the helical groove relative to the filed index tooth, thereby advancing the cutting edge to form a percutaneous hole through the tissue surrounding the patient's ear canal.

The hollow shank of the hole forming tool contains a lumen which accommodates a rod adapted to be pushed distally through the shank for ejecting any tissue captured by the shank distal end.

The preferred instrument set further includes an inserter instrument comprising a handle defining a bore for receiving the implantable device. The inserter handle works in cooperation with the cannula and a pusher tool. The pusher tool is used to push the implant out of the inserter handle and along the cannula lumen to a position proximate to the patient's ear canal to project the implant's stud percutaneously into the ear canal.

The preferred instrument set preferably also includes a speculum useful by the physician during the implant procedure for spreading the patient's ear canal to enhance visibility while also presenting an anvil, or cutting board, surface for the tool cutting edge to engage.

Further, a push-back tool is preferably provided which the physician can insert into the patient's ear canal to engage and properly position the percutaneously extending stud.

BRIEF DESCRIPTION OF THE FIGURES

FIGS. 5A, 5B, 5C, and 5D illustrate the preferred cannula where

FIGS. 8A, 8B, 8C, and 8D illustrate the preferred hole former where

DETAILED DESCRIPTION

Figure 1:
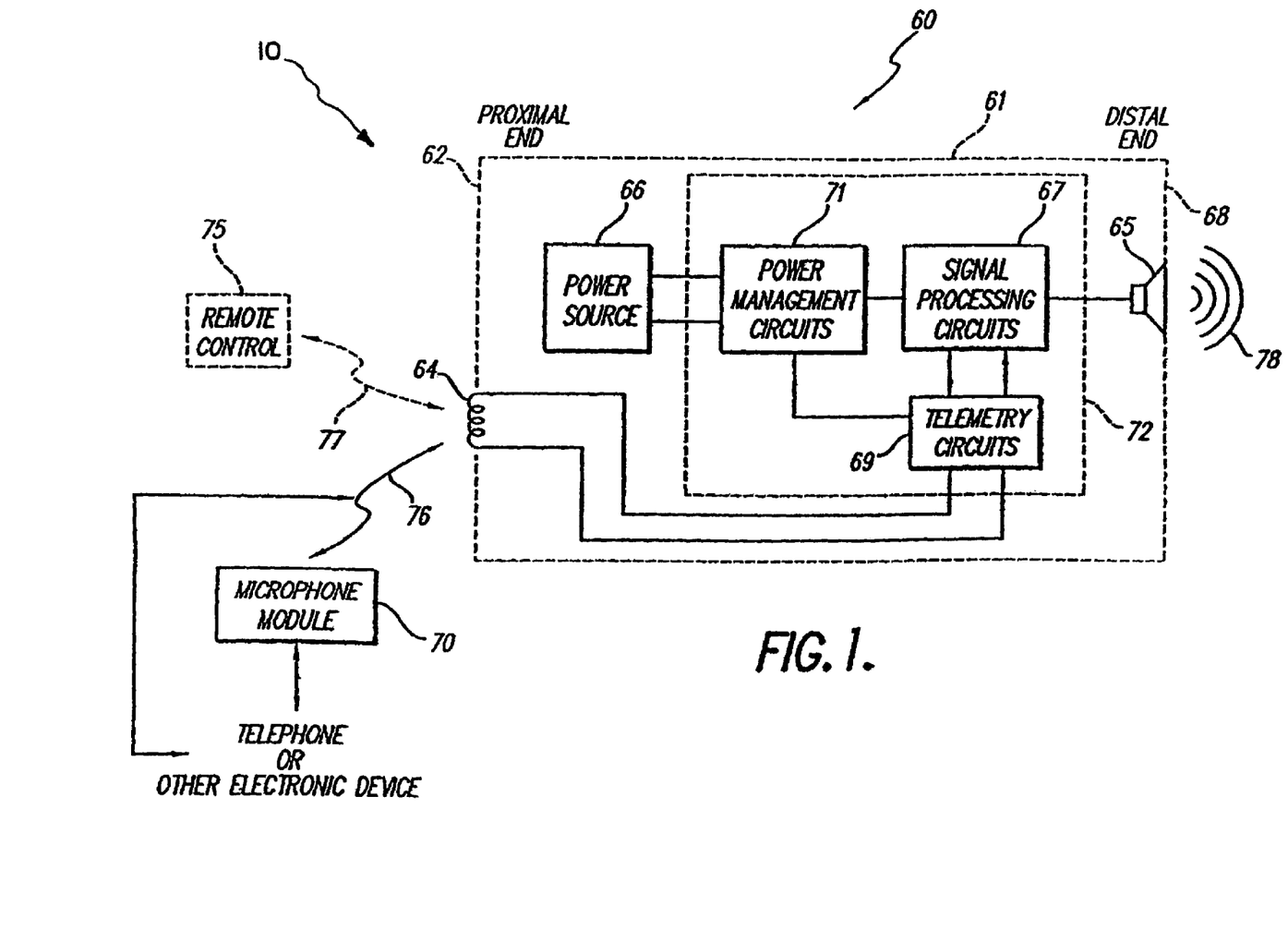
FIG. 1 is a block diagram of an exemplary hearing aid system including a microphone module and an implantable electroacoustic transducer device for projecting sound energy into a patient's ear canal.
Figure 2A:
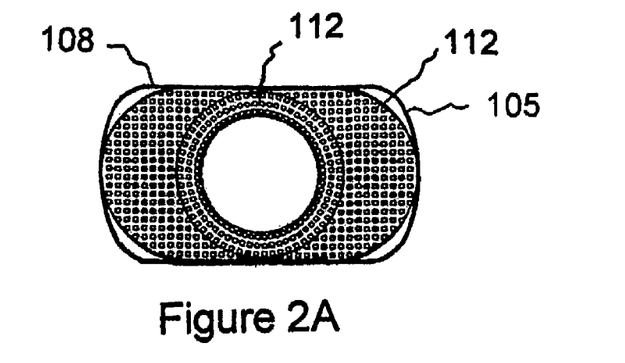
FIGS. 2A, 2B, and 2C are respectively end, top, and side views of a preferred implantable device in accordance with the invention.
Figure 2B:
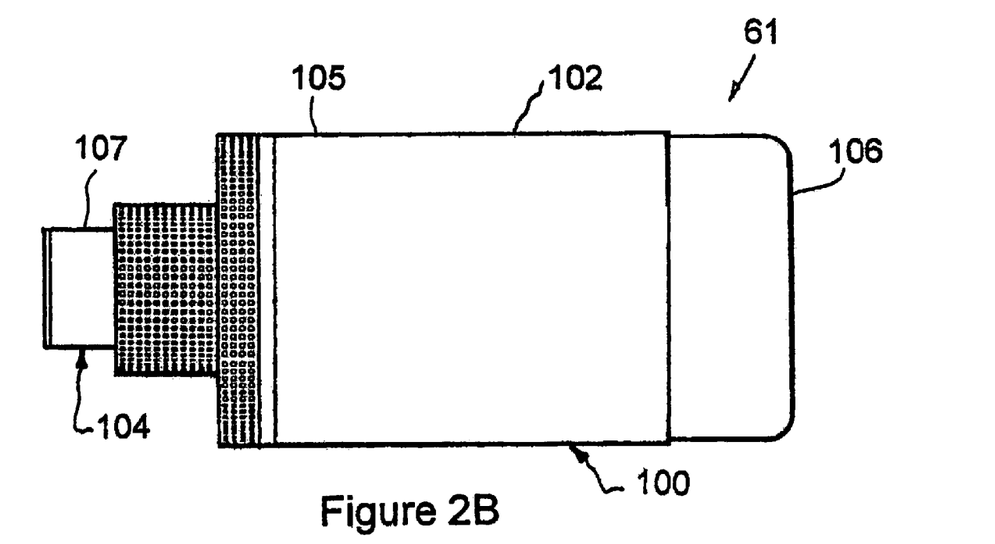
Figure 2C:
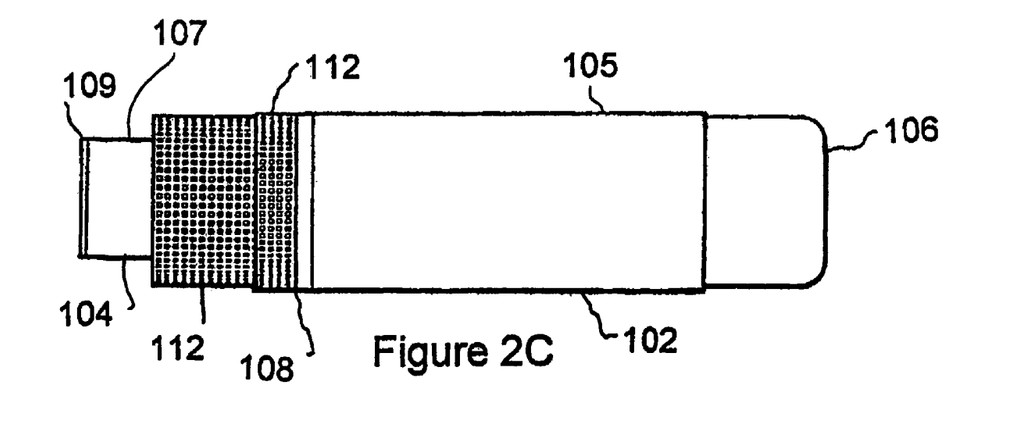

Attention is initially directed to FIG. 1 which illustrates a hearing aid system 10 of the type disclosed in aforementioned U.S. international application PCT/US2003/0353348, which system can advantageously employ the teachings of the present invention. The exemplary system 10 includes an implantable device (or "implant") 60 comprising a housing or case 61. The structural aspects of a preferred housing 61 are illustrated in FIGS. 2A, 2B and 2C to be discussed hereinafter. In addition to the implant 60, the exemplary system 10 contemplates utilization of an external microphone module 70 capable of communicating via a telemetry link 76 with an antenna 64 mounted within the implant housing 61. The antenna 64 is coupled to electronic circuitry 72 contained within the housing 61. More particularly, the antenna 64 is coupled to signal processing circuitry 67 via telemetry circuitry 69. The implant housing 61 also includes a power source 66, typically a battery, for supplying power, via power management circuitry 71, to the signal processing circuitry 67 and telemetry circuitry 69. The signal processing circuitry 67 drives an electroacoustic transducer 65, e.g., a speaker, to produce sound energy 78.

In typical operation of the exemplary system 10 of FIG. 1, the microphone module 70 is worn externally by a patient and converts sound energy to an RF telemetry signal 76 representing audio information in analog or digitally encoded form. This RF signal is transmitted to the implant antenna 64 and coupled to the electronic circuitry 72 for processing. The telemetry circuitry 69 includes a receiver (not shown) to acquire, filter, and process the incoming signal. The antenna 64 may additionally receive charging electromagnetic energy to charge the power source 66. This energy is transmitted via the telemetry circuitry 69 to the power management circuitry 71. The system 10 may also include a remote control device 75, e.g., a hand held controller, which can be used by the patient to supply commands, via antenna 64, to the signal processing circuitry 67 for affecting various operational parameters such as volume, equalization profile, etc.

FIGS. 2A, 2B and 2C illustrate a preferred implant housing 61 in accordance with the present invention. The housing 61 basically comprises a hollow structure 100 comprised of a body portion 102 and a distally extending stud 104. The body portion 102 comprises an outer wall defining a peripheral wall surface 105 and a proximal end wall surface 106.

The peripheral surface 105 extends from the proximal end wall surface 106 to a lateral shoulder surface 108. Stud 104, defining peripheral wall surface 107, extends distally from the shoulder surface 108 terminating at distal end wall surface 109. The housing peripheral surface 105 preferably defines a noncircular cross-section, e.g., oval, for mating with a similarly shaped surgical instrument lumen to be described hereinafter. The stud peripheral surface 107 preferably defines a circular cross-section. As can be seen in FIGS. 2A, 2B and 2C, the housing surfaces, e.g., peripheral surface 107 and lateral shoulder surface 108 preferably carry a layer of porous material 112, e.g., titanium mesh, for promoting tissue ingrowth for retaining the housing 61 in place after implantation.

Figure 3:
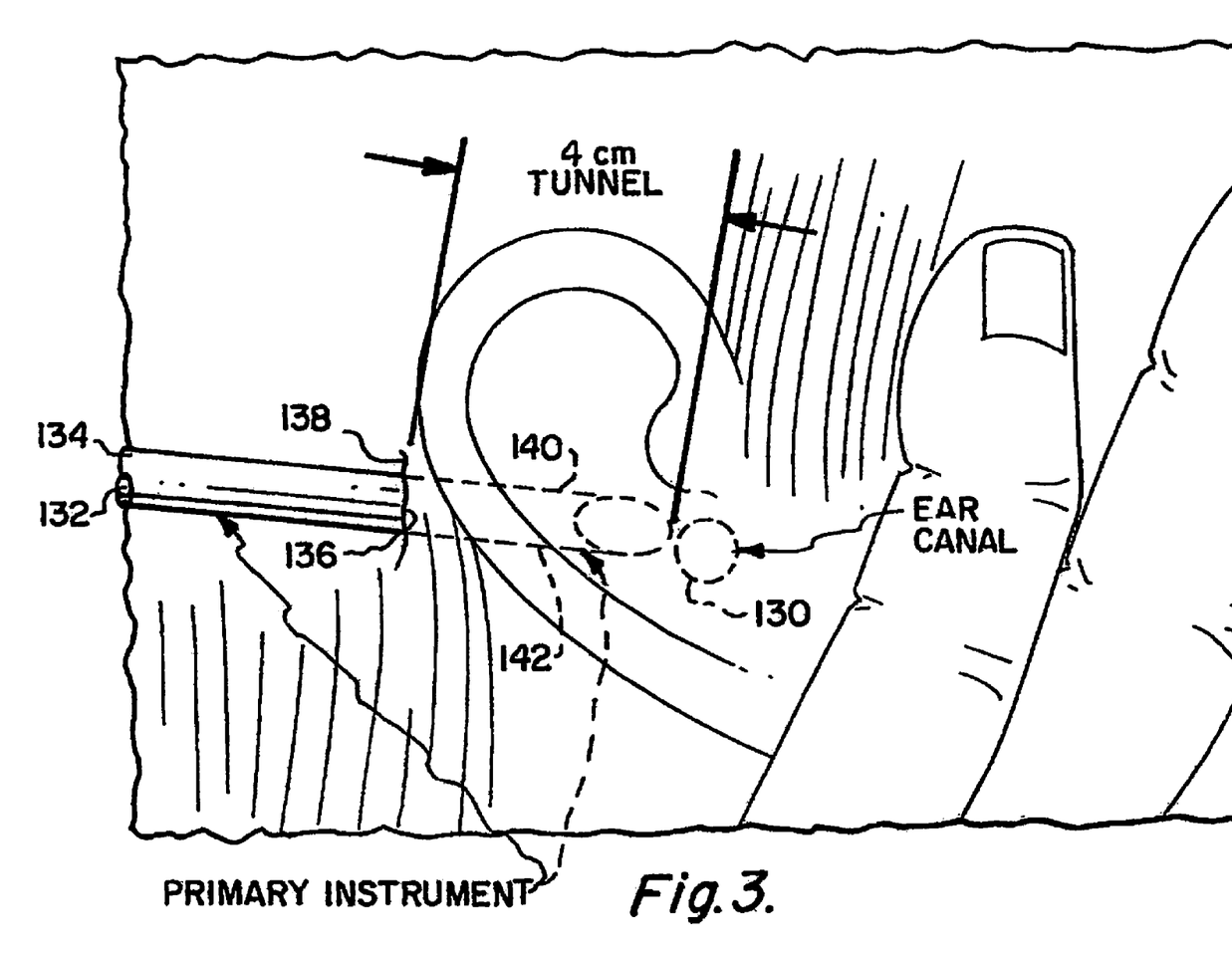
FIG. 3 schematically illustrates a patient's ear area depicting the position of the ear canal and indicating the use of a cannula instrument in accordance with the invention for subcutaneously implanting the transducer device to project sound from a stud extending percutaneously into to the patient's outer ear canal.

Attention is now directed to FIG. 3 which generally illustrates the ear area of a patient, and the position of the patients ear canal 130. FIG. 3 also depicts the distal portion of a hollow shaft 132 of a surgical instrument (cannula) 134 to be discussed in detail hereinafter. As will be described, the instrument 134 is used to tunnel through the patients subcutaneous tissue to create a path for transporting the implant housing 61 to a recess adjacent to the ear canal 130. More particularly, as will be discussed hereinafter, in accordance with the present invention, the distal end 136 of shaft 132 is advanced along a path 140 from an incision 138 behind the patients pinnace to an implant site proximate to the ear canal 130. Thereafter, the hollow shaft 132 is used to transport the implant housing 61 to the implant site such that the implant housing stud 104 can percutaneously extend into the canal 130 for projecting sound energy directly into the patient's ear canal.

Figure 4:
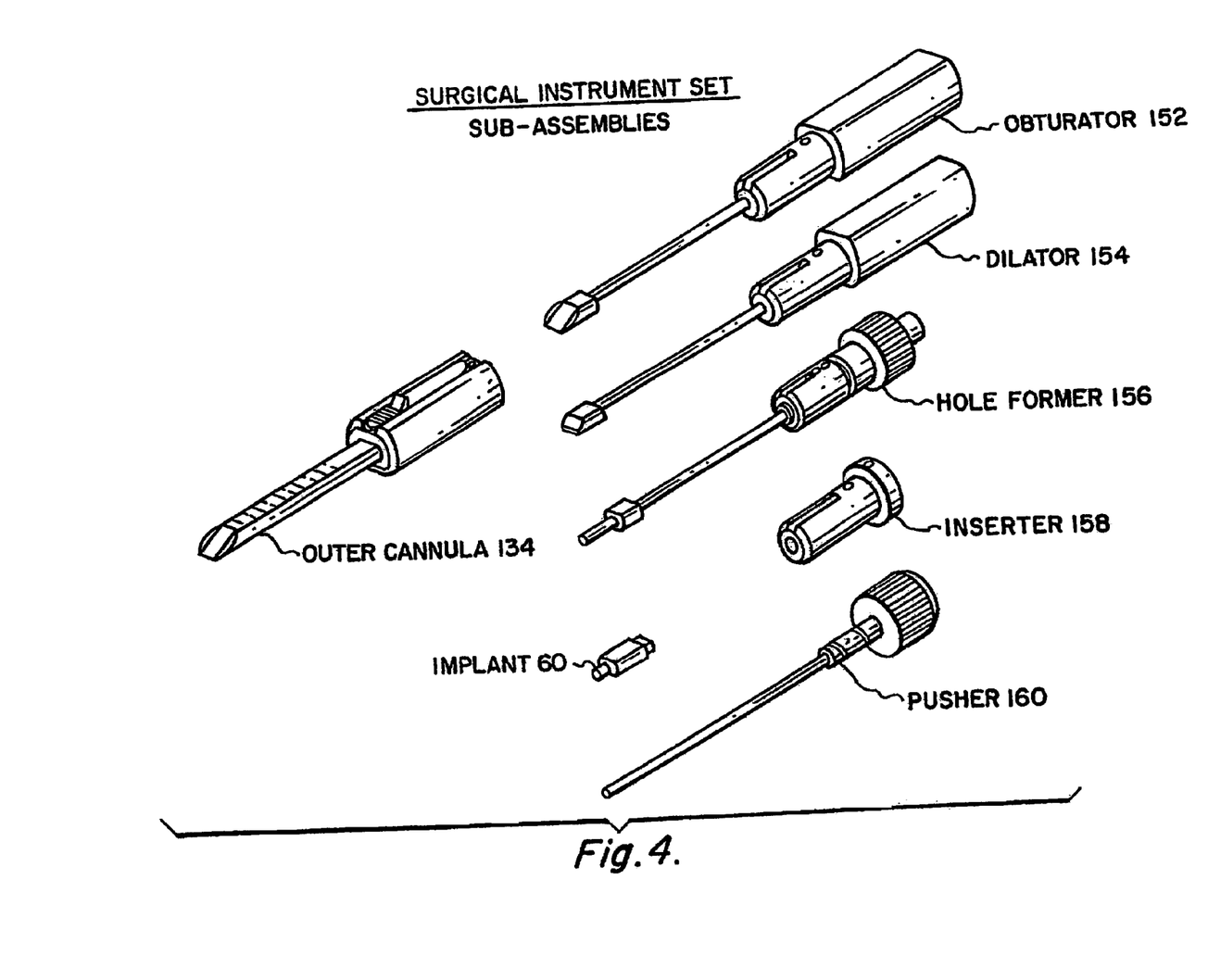
FIG. 4 illustrates members (i.e., a cannula, an obturator, a dilator, a hole former, an implant inserter, and a pusher) of a preferred surgical instrument set in accordance with the invention useful for implanting the device of FIGS. 2A, 2B, and 2C.

Attention is now directed to FIG. 4 which illustrates perspective views of members of a preferred surgical instrument set useful for enabling a physician to readily implant the device 60. The preferred instrument set includes the cannula 134, an obturator 152, a dilator 154, a hole former 156, an implant inserter 158 and a pusher 160. Additional instruments useful in the implant procedure may include a speculum configured to provide an anvil or cutting board surface (FIGS. 10A, 10B, 11) and a positioning, or push-back tool (FIG. 12).

Figure 5A:
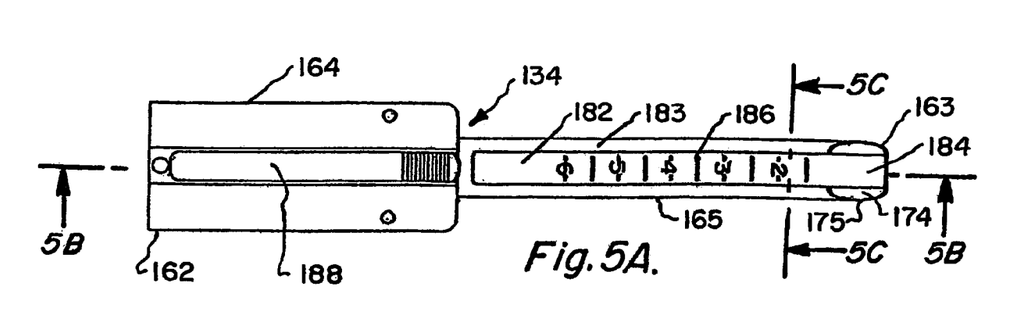
FIG. 5A is a top view.
Figures 5B, 5C, 5D:
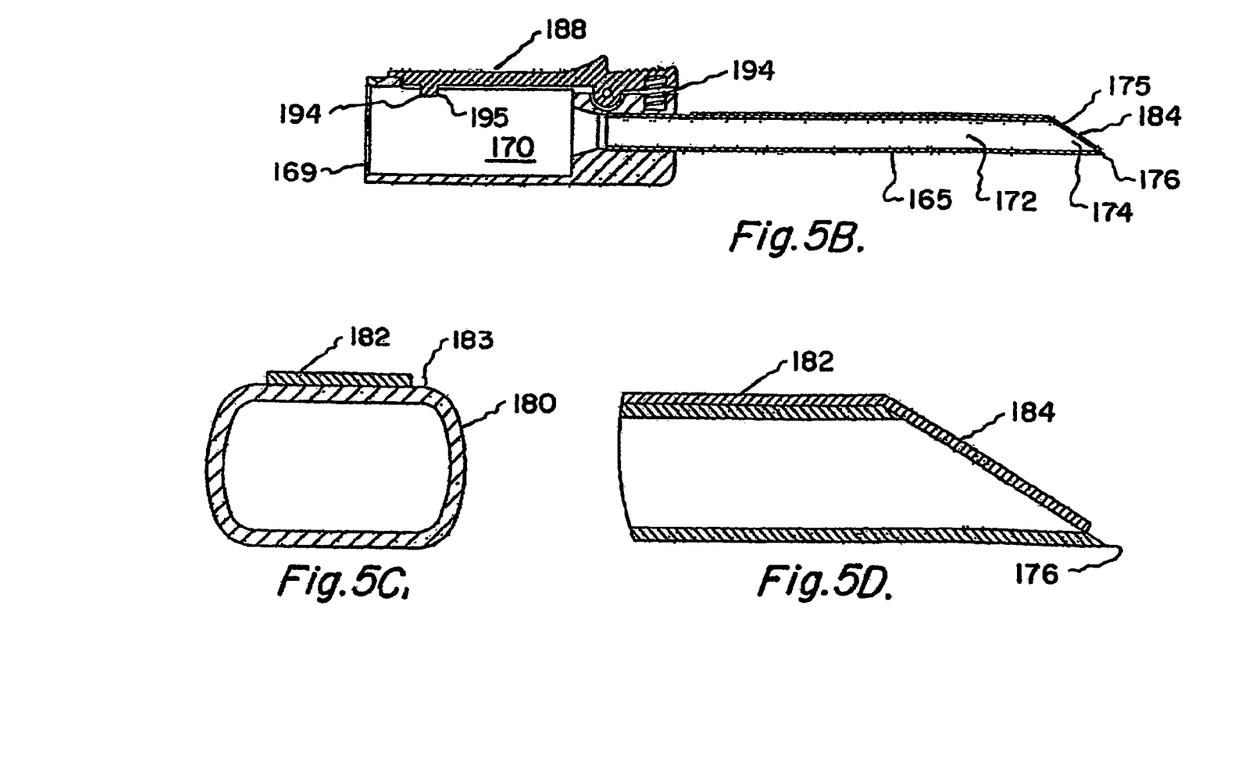
FIGS. 5B and 5C are sectional views taken substantially along planes 5B-5B and 5C-5C.
FIG. 5D is an enlarged view of the distal end of the cannula.

Attention is now directed to FIGS. 5A and 5B which illustrate the preferred cannula 134 for forming a tunnel 140 as shown in FIG. 3 for transporting the implant device 60 to a desired location proximate to the patient's ear canal 130. The cannula 134 having a proximal end 162 and a distal end 163 is comprised of a handle 164 and an elongate shaft 165. An entrance opening 169 at the proximal end 162 opens into an interior bore 170. The bore 170 communicates with interior lumen 172 extending through the elongate shaft 165 to an exit opening 174 at the cannula distal end 163.

The distal end 163 of shaft 165 is preferably beveled along plane 175 and forms a chisel edge 176. As shown in FIG. 5C, the shaft wall 180 preferably has a noncircular, e.g., oval, cross-section. Optionally, a thin strip of flexible metal 182 is provided to overlay the upper exterior surface 183 of shaft 165 and bend downwardly at its distal end to form a door 184. The door 184 overlays and normally substantially closes the lumen exit opening 174. The strip 182 is preferably sufficiently flexible to enable the door 184 to be pushed open by a member from within the lumen 172, as will be discussed hereinafter.

Markings 186, comprising a linear scale, are preferably formed along the upper exterior shaft surface 183 and/or the surface of strip 182, for indicating to the physician the depth of subcutaneous penetration of the shaft distal edge 176.

The cannula handle 164 preferably includes a finger operated latch 188 mounted for pivotal movement around pin 190. A spring 192 normally biases the latch 188 in a counter clockwise direction (as viewed in FIG. 5B) to urge an index tooth 194 through opening 195 into bore 170. As will be seen hereinafter, the index tooth 194 is used to operatively latch various members of the preferred instrument set (FIG. 4) to the cannula 134 in the course of performing the implant procedure.

Figure 6A:
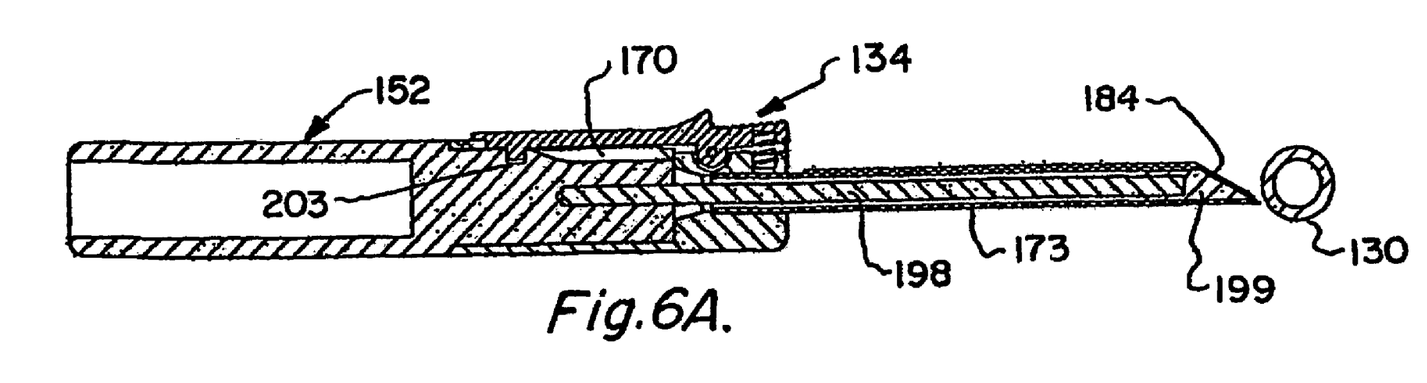
FIG. 6A illustrates the preferred obturator extending through the cannula shaft and FIG. 6B depicts the cannula/obturator tunneling through tissue to position the cannula distal end proximate to a patient's ear canal.

Attention is now called to FIG. 6A which depicts the obturator 152 mounted in the cannula 134. Note that the obturator comprises a handle 196 having a rod 198 extending therefrom. The rod carries a dilator block 199 at its distal end which is insertable through cannula bore 170 for passage through lumen 172 for positioning adjacent to door 184. The block 199 has a cross-section shaped and dimensioned to substantially fully occupy the lumen 172 and is beveled to conform to the bevel plane 175 at the front of cannula shaft 165. When the obturator rod 198 and block 199 are inserted through bore 170, shoulder 200 on the obturator handle 196 engages interior surface 202 of cannula 134 and/or index tooth 194 falls into a recess 203 in the obturator handle. This action locates block 199 immediately behind the door 184.

With the obturator 152 mated with the cannula 134 (FIG. 6A), the physician will typically begin the implant procedure by forming a 2 cm skin incision 138 behind the pinnace, approximately 4 cm posterior to the ear canal 130 at an angle of roughly 30° to a horizontal line radiating from the center of the ear canal.

Figure 6B:
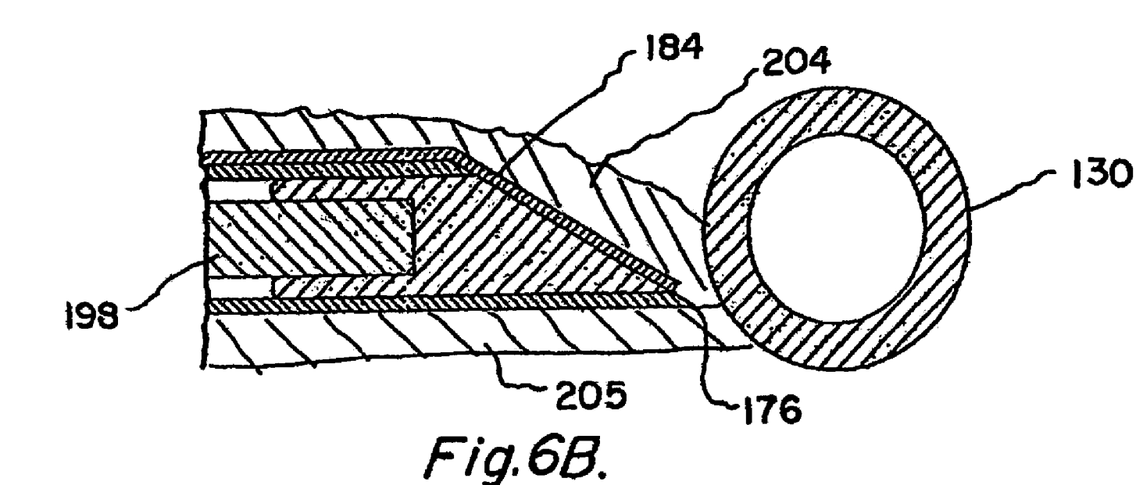

The physician will then use the mated cannula/obturator to tunnel from the skin incision to a location proximate to the ear canal. The chisel edge 176 functions to separate subcutaneous tissue 204 (FIG. 6B) from bone 205 as the physician presses the handle 196 to advance edge 176 toward the ear canal. Tunneling typically continues until the physician observes tenting or skin protrusion within the ear canal. The depth markings 186 can be used as a guide during tunneling to assist the physician. It is preferable that tunneling terminate when the edge 176 is approximately 2-3 mm short of the ear canal. During tunneling, the door 184 simply lays flat against the beveled end of block 199 and cannula shaft 165.

Figure 7A:
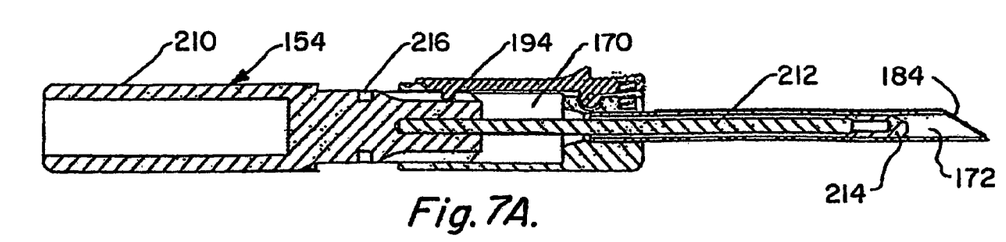
FIGS. 7A and 7B illustrate the preferred dilator extending through the cannula shaft and FIGS. 7C and 7D are enlarged views showing the cannula distal end.
Figure 7B:
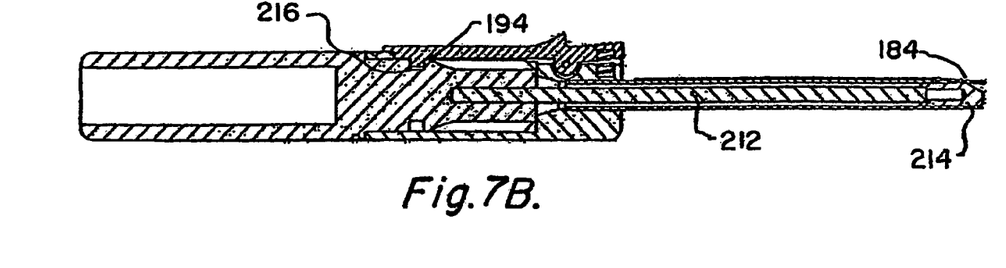
Figure 7C:
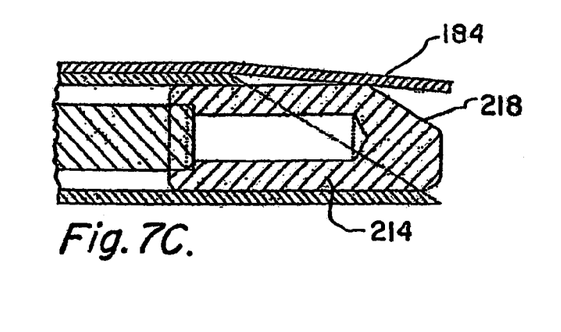
Figure 7D:
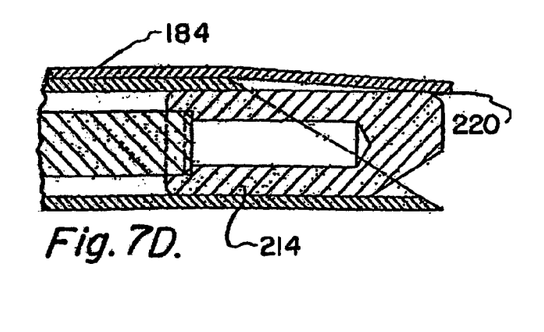

After the edge 176 reaches the desired location, the obturator 152 is withdrawn from the cannula proximal end leaving the cannula 134 in place. The physician then will insert the dilator 154 through the cannula lumen 172 as shown in FIG. 7A. The dilator 154 is comprised of a handle 210 and a forwardly projecting shaft 212. The shaft 212 terminally carries a dilator block 214. The dilator shaft 212 and block 214 are inserted through the cannula bore 170 and shaft lumen 172 towards the door 184. Note in FIG. 7A that the dilator handle 210 defines a recess, or groove, 216 positioned to receive cannula index tooth 194. FIG. 7A depicts the dilator 154 partially inserted into cannula 134 whereas FIG. 7B shows the dilator fully inserted with the index tooth 194 clicked into the dilator groove 216. Note in FIG. 7B that with the index tooth 194 and groove 216 engaged, the dilator shaft 212 positions the block 214 so that it opens the door 184. The dilator block 214 is tapered at surface 218 and can be used in either of two opposite orientations, respectively shown in FIGS. 7C and 7D. In the first orientation (FIG. 7C), the tapered surface 218 is shown facing the door 184. In the second orientation (FIG. 7D), the tapered surface 218 is remote from the door 184 and instead the square surface 220 of the dilator block 214 faces the door. The function of the dilator 154 is to push tissue away from the open distal end of the cannula 134 so that the subsequently used hole former 156 need only cut through tissue directly in front of the cannula edge 176. Depending upon the nature of the tissue to be dilated, the physician may choose to use the dilator block 218 as shown in FIG. 7C for gentle dilation or as shown in FIG. 7D for more aggressive dilation.

Figure 8A:
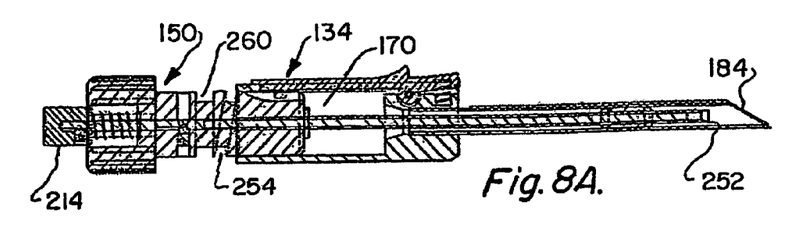
FIG. 8A shows the hole former inserted in the cannula shaft but not yet engaged with the cannula index tooth.
Figure 8B:
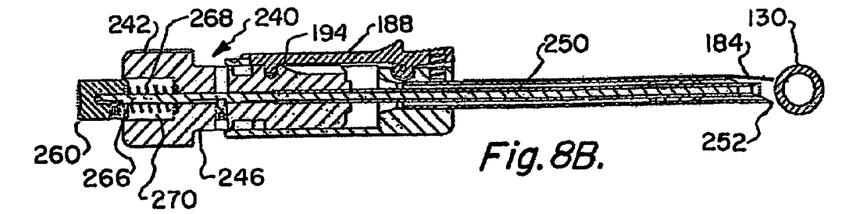
FIG. 8B shows the index tooth engaged with a threaded groove on the hole former.
Figure 8C:
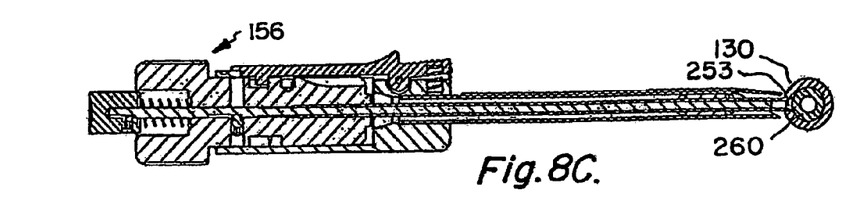
FIG. 8C shows the hole former having advanced along the cannula shaft to cause its distal cutting edge to form a percutaneous hole opening into the ear canal.
Figure 8D:
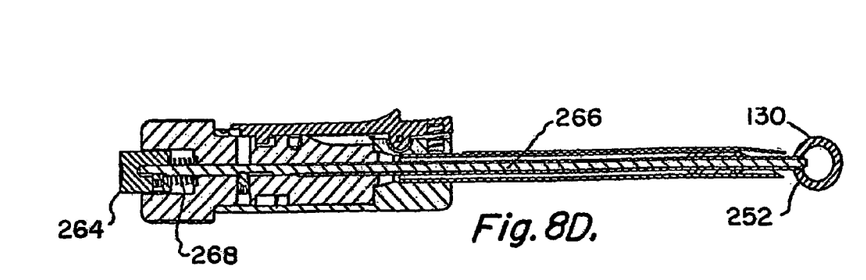
FIG. 8D shows a rod extending through the hole former shaft for ejecting tissue from its distal end.

After dilation of the subcutaneous tissue, the dilator 154 is removed from the cannula 134 which remains in situ. Thereafter, the hole former 156 is installed into the cannula 134. FIG. 8A shows the hole former 156 partially inserted into the cannula 134. FIG. 8B shows the hole former 156 fully inserted into the cannula but with its cutting edge still in a retracted non-cutting position. FIG. 8C shows the hole former 156 with its cutting edge advanced for cutting a percutaneous hole into the ear canal. FIG. 8D shows a rod within the hole former shank being advanced to eject any tissue captured by the shank cutting edge.

More particularly, the hole former 156 is comprised of a handle 240 including an enlarged knurled portion 242 and a reduced portion 246. A hollow shank 250 extends distally from the reduced portion 246. The shank 250 at its distal end is provided with a cutting edge 252 preferably forming a circular periphery.

A helical groove 254 is formed on the outer surface of the reduced handle portion 246. The groove 254 is dimensioned to accommodate the index tooth 194 carried by the cannula latch 188. In use, the hole former 156 is inserted through the cannula entrance opening 169 into bore 170 until the index tooth 194 clicks into a distal thread of the helical groove 254, as shown in FIG. 8B. When so engaged, the distal end of the shank 250 opens the door 184 placing the cutting edge 252 a short distance from the tissue surrounding the ear canal 130. The physician is then able to axially rotate the handle 242 to thread groove 254 with respect to the fixed tooth 194 to axially advance the shank 250 and thus move the cutting edge 252 to the ear canal wall. In order to cleanly cut a hole 253 through the ear canal wall, it is preferable to insert an anvil, or cutting board, surface 260 within the ear canal for the cutting edge 252 to bear against. In use, the physician will carefully observe the interior of the ear canal as he rotates handle 242 to advance the cutting edge 252. The helical groove 254 is typically formed so that the total axial movement available from FIG. 8B to FIG. 8C is small, e.g., 5-6 mm. Typically, the physician inserts the anvil when he first observes tissue tenting within the ear canal. Speculum embodiments providing the anvil, or cutting board, surface will be discussed later in conjunction with FIGS. 10A, 10B, and 11.

The helical coil 254 is preferably configured so that an initial amount of rotation axially advances cutting edge 252 (mode 1) and additional rotation freely spins the cutting edge (mode 2). That is, once the threaded groove 254 has advanced to the position shown in FIG. 8C, the handle 242 can be rotated back and forth to freely spin the cutting edge 252 to cleanly cut the hole through to the ear canal. Although reference has been made to "cutting" the hole, it should be understood that the hole can be alternatively formed, e.g., punching.

Once the hole has been formed any tissue captured within the lumen of the shank 250 can be ejected by pressing an ejector button 264 mounted adjacent the handle portion 242. Note that the ejector button is secured to an axial rod 266 which extends through the lumen of hollow shank 250. A spring 268 retained in recess 270 in handle portion 242 biases the button 264 to the left as shown in FIGS. 8A, 8B, and 8C. Note however in FIG. 8D that the button 264 has been manually pushed to the right into the recess 270, compressing spring 268, to thrust rod 266 forwardly past the shank cutting edge 252. This action ejects any tissue plug captured within the shank 250. The physician then can readily retrieve the plug from the ear canal with forceps. Typically, the physician prefers to eject the plug into the ear canal before removing the hole former 156 from the cannula 134 so that the plug is not lost when the cannula is subsequently removed.

Figure 9A:
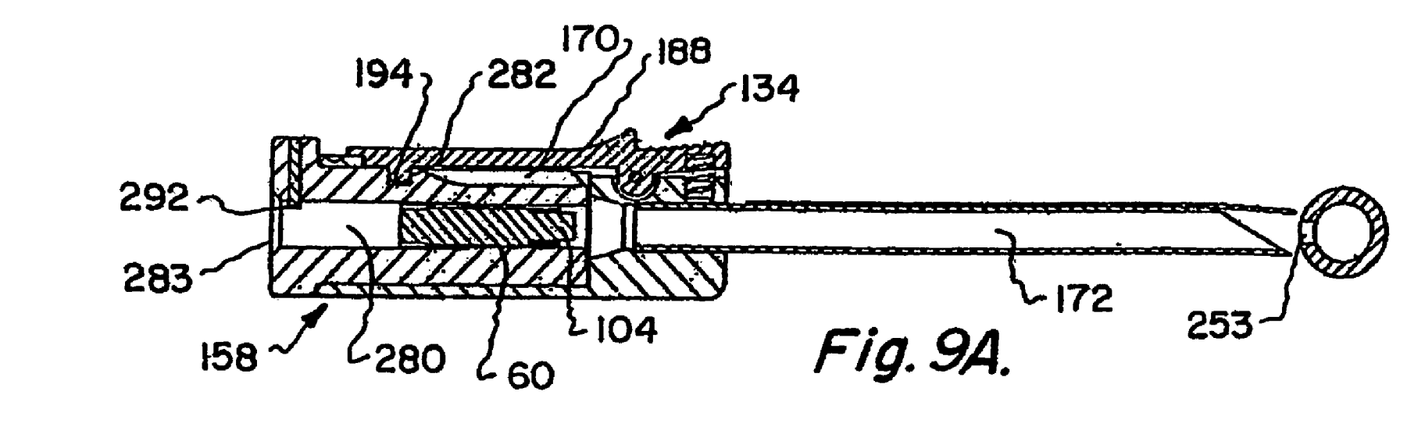
FIGS. 9A and 9B illustrate the preferred inserter and pusher for transporting the implant through the cannula shaft to a position proximate to the patient's ear canal with the implant's distally projecting stud extending into the ear canal.
Figure 9B:
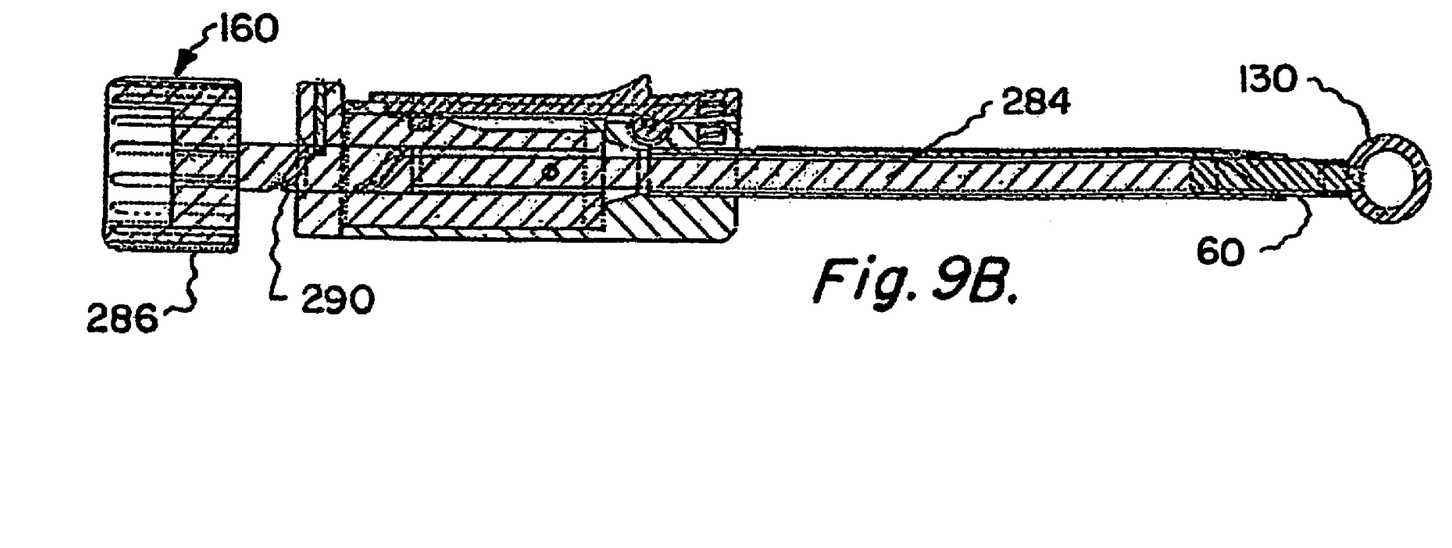

After the hole former 156 is removed from the cannula 134, the inserter 158 is inserted into the cannula bore 170 as depicted in FIG. 9A. Prior to installing the inserter 158 into the cannula, the implant housing 61 is placed within a bore 280 of the inserter 158. Note that the inserter has an exterior recess 282 formed thereon for receiving the index tooth 194 carried by the spring urged latch 188. The inserter bore 280 is open at its proximal end 283 so that the shaft 284 of the aforementioned pusher 160 can be inserted therethrough as shown in FIG. 9B. The pusher shaft 284 is attached to a pusher handle 286. The shaft 284 is preferably provided with a threaded helical groove 290 configured to mate with a tooth 292 carried by the inserter and extending into the inserter bore 280. Thus, by turning the pusher handle 286 relative to the inserter 158, the pusher shaft 184 will advance axially as the helical groove 290 is threaded relative to the tooth 292. This axial advance enables the shaft 284 to transport the implant device 60 through the cannula lumen 172 to a position proximate to the ear canal. As previously mentioned, the cannula lumen 172 and the implant device housing preferably have corresponding non-circular cross-sections which assures that the device housing does not rotate as it is transported through the cannula lumen 172. The device 60 will arrive at the ear canal 130 properly positioned for the device stud 104 to project through the percutaneous hole 253 previously formed in the ear canal as represented in FIG. 8C.

Figure 10A:
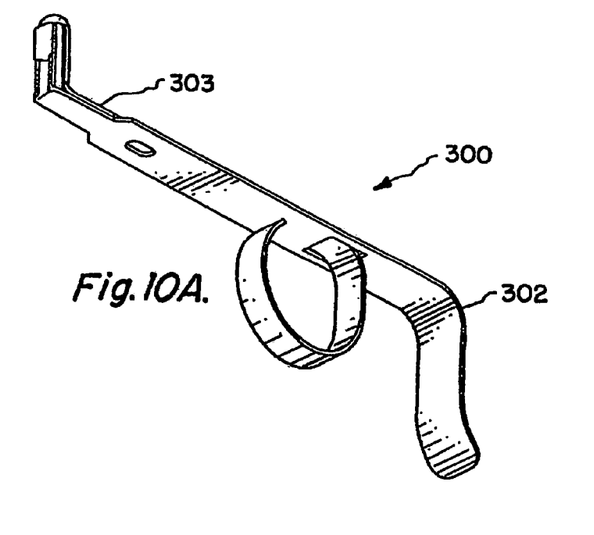
FIGS. 10A and 10B illustrate a speculum useful by a physician during the implantation procedure for stretching the patient's ear canal to enhance visibility while also presenting an anvil, or cutting board, surface for the hole former cutting edge to engage.
Figure 10B:
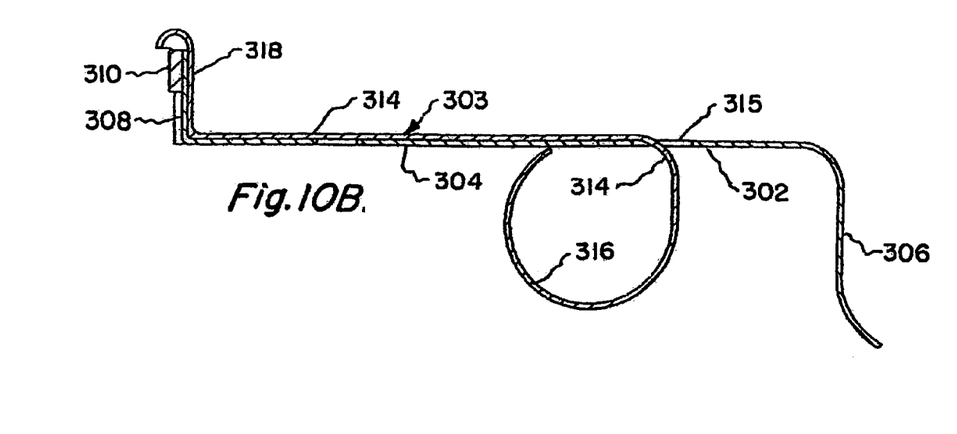

Attention is now directed to FIGS. 10A and 10B which illustrate a preferred right angle speculum 300 useful by the physician to spread the patient's ear canal for better visibility when using the aforedescribed hole former tool 156. The speculum 300 is comprised of a base member 302 and a slide member 303. The base member 302 comprises a flat metal strip having an intermediate portion 304, a downwardly bent rear portion 306, and an upwardly bent forward portion, or jaw, 308. The jaw 308 carries an anvil, or cutting board, member 310.

The speculum 300 slide member 303 includes a flat intermediate portion 314 which overlays the base member intermediate portion 304. The rear portion of slide member 303 is bent downwardly at 314 extending through base member slot 315 to form a loop 316 for receiving a user's index finger. The forward end of slide member 314 is bent upwardly to form a jaw 318.

The physician will typically use the speculum 300 in conjunction with using the hole former 156 by placing the speculum jaws 308 and 318 in the patient's ear canal. The cutting board 310 is aligned with the anticipated location of the percutaneous hole 253. The physician will then place his thumb against the rear portion 306 of base member 302 and his index finger through loop 316. By squeezing the thumb and index finger, the slide member 303 will move rearwardly (to the right as viewed in FIG. 10B) to spread jaws 308 and 318. The spreading of the jaws will spread the ear canal to improve visibility and also place the cutting board in a position to be engaged by the cutting edge 252 to form a clean percutaneous hole.

Figure 11:
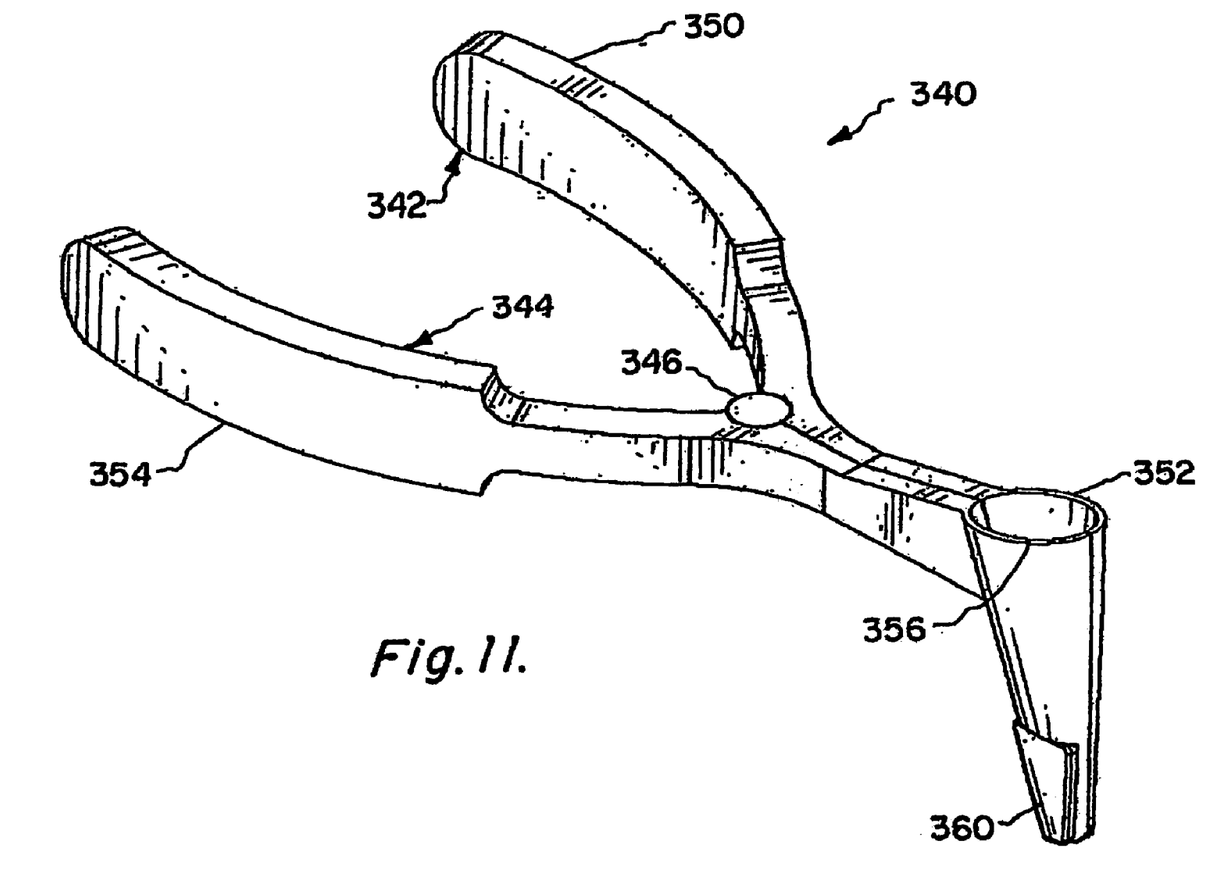
FIG. 11 illustrates an alternate speculum for presenting a cutting board surface to the hole former cutting edge.
Figure 12:
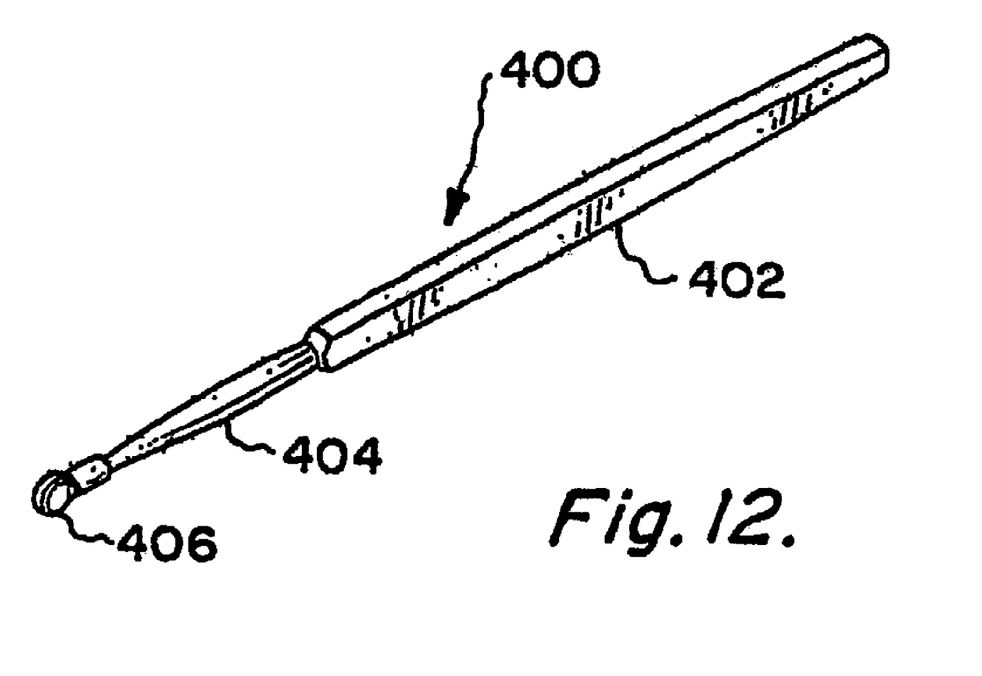
FIG. 12 illustrates a push-back tool useful for positioning the percutaneous stud in the patient's ear canal.

FIG. 11 illustrates an alternative speculum 340 including members 342 and 344 mounted for hinged movement around pin 346. Member 342 is comprised of a handle portion 350 and a jaw portion 352. Member 344 is similarly comprised of a handle portion 354 and a jaw portion 356.

In use, the physician will insert the jaw portions 352 and 356 into the patient's ear canal. By squeezing the handle portions 350 and 354, the jaw portions 352 and 356 move apart to spread the patient's ear canal to increase visibility. In accordance with the present invention, at least one of the jaw portions carries an anvil, or cutting board, member 360 to provide a surface for engagement by the hole former cutting edge as represented in FIG. 8C.

FIG. 12 illustrates a positioning or push back tool 400. The tool 400 is comprised of a handle 402 and a shaft 404 carrying a flat disk 406 at its distal end. The tool 400 can be used by the physician by inserting the disk 406 into the patient's ear canal to engage the percutaneously extending implant stud 104 to push back and properly position the stud end face in the ear canal.

Figures 13A, 13B:
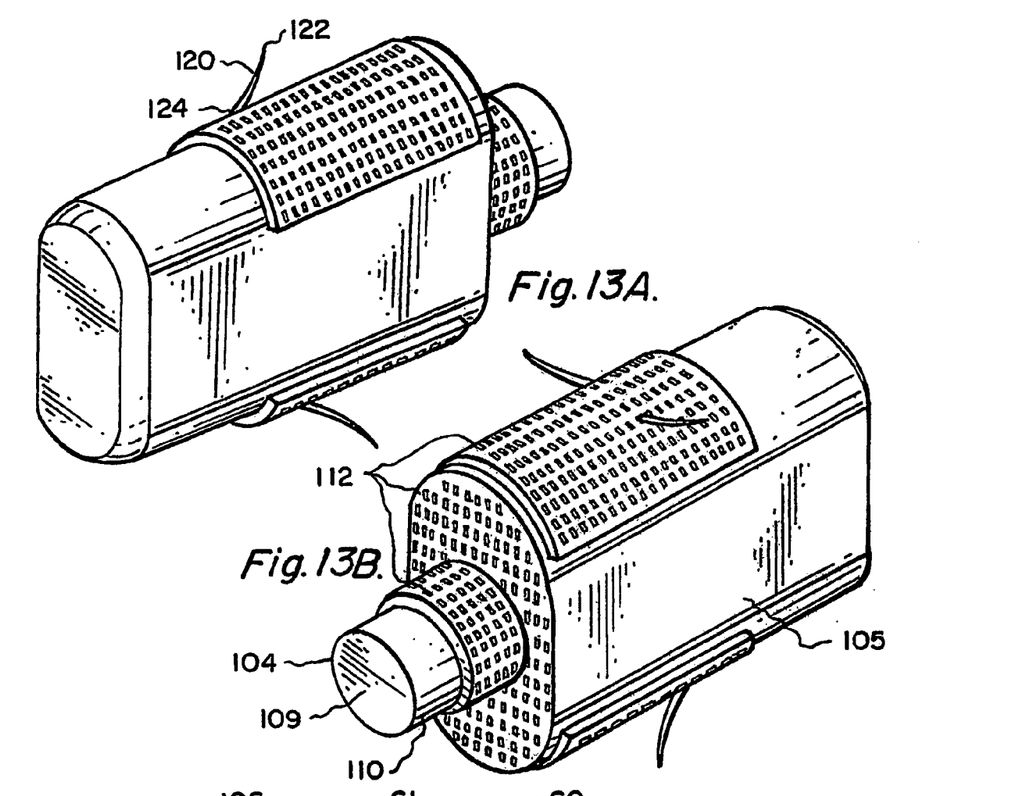
FIGS. 13A, 13B, and 13C illustrate an alternative implant in accordance with the invention characterized by anchors carried by the implant housing for anchoring the housing in body tissue.
Figure 13C:
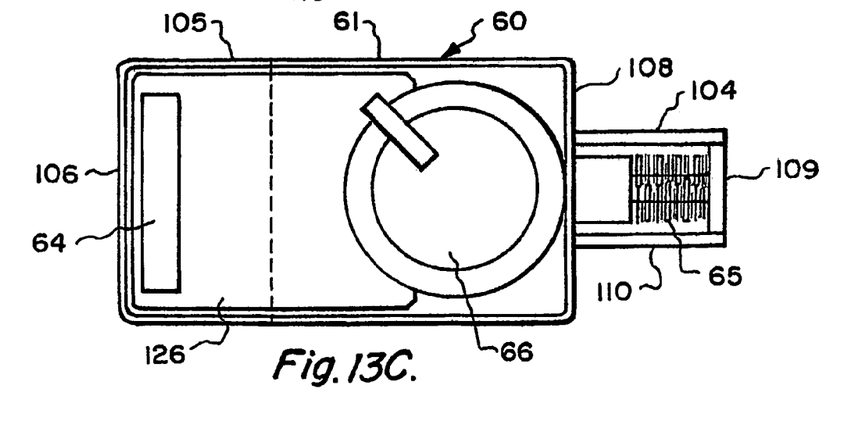

FIGS. 13A, 13B and 13C illustrate a modification of the implant housing 61 shown in FIGS. 2A, 2B and 2C to achieve enhanced anchoring if desired. The housing 61 of FIGS. 13A, 13B, 13C utilizes additional porous material 112 extending proximally from the shoulder 108 over a greater area of the peripheral surface 105 of body portion 102. Additionally, to facilitate device anchoring prior to adequate tissue growth into the porous layer 112, one or more fixation arms, or anchors, 120 is provided. Each arm 120 has a first free end 122 and a second end 124 secured to the housing body portion 102. Each arm 120 is preferably formed of flexible material so it can be pressed to a retracted position against the peripheral surface of body portion 102 prior to being ejected from the cannula lumen, as represented in FIG. 9B. As depicted in FIGS. 13A, 13B, and 13C, the arms 120 will deploy by extending outwardly for engaging subcutaneous body tissue to better anchor the housing 61.

FIG. 13C schematically depicts a sectional view through the housing 61 to show an exemplary placement of components within the housing. More particularly the housing 61 encloses a sealed internal compartment containing at least one circuit board 126. The circuit board 126 can carry a planar antenna 64 connected to a power source 66 in the form of a disc shaped battery. An electroacoustic transducer 65 is mounted within the portion of compartment 125 extending into stud 104 for projecting sound energy through stud end wall 109.

From the foregoing, it should now be appreciated that an improved hearing aid system has been disclosed herein which enables the implantation of a hearing aid in a tunnel or recess adjacent to a patient's ear canal for positioning a sound transducer to project sound through a percutaneous hole directly into a patient's outer ear canal. By utilization of the simple instrument and procedure disclosed herein, the described hearing aid can be readily deployed in a physician's office procedure with little or no insult to the tissue adjacent to the ear canal.

Although a specific embodiment of the invention has been disclosed herein, it should be recognized that variations and modifications will occur to those skilled in the art well within the spirit and intended scope of the invention as defined by the appended claims.

The invention claimed is:

1. A method for implanting a hearing aid in a patient so as to extend percutaneously into the patient's outer ear canal, said method comprising:
   providing an elongate shaft having an outer wall surrounding at least one elongate lumen extending through said shaft to a distal end;
   tunneling said shaft from a location behind the patient's pinna to a position said shaft distal end in subcutaneous tissue proximate to said patient's ear canal;
   inserting an elongate tool through said lumen so as to position a tool cutting edge proximate to said shaft distal end;
   advancing said tool cutting edge past said shaft distal end to form a percutaneous hole opening into said ear canal;
   providing a hearing aid housing having a stud projecting therefrom; and
   transporting said housing through said lumen to said shaft distal end to position said stud in said percutaneous hole opening into said ear canal.

2. The method of claim 1 wherein a porous layer is provided on the peripheral surface of at least a portion of said housing for promoting tissue ingrowth.

3. The method of claim 1 wherein said tunneling step includes providing an obturator to close said lumen proximate to said shaft distal end.

4. The method of claim 1 further including inserting an anvil in said patient's ear canal; and wherein
   said step of advancing said tool cutting edge includes engaging said cutting edge against said anvil.

5. The method of claim 1 wherein said housing carries at least one anchor configured for movement between a retracted position and a deployed position;
   and wherein when said housing is being transported through said lumen said anchor is retracted and when said housing engages said subcutaneous tissue said anchor is deployed to retain said housing adjacent to said percutaneous hole.

6. The method of claim 1 wherein said step of providing said elongate shaft includes providing a shaft having a flat bevel edge at its distal end for facilitating the separation of skin from bone while tunnelling.

7. The method of claim 1 wherein said step of providing an elongate shaft includes providing a shaft outer wall having a noncircular cross-section.

8. The method of claim 1 wherein said step of providing an elongate shaft includes providing an elongate lumen having a noncircular cross-section.

9. The method of claim 8 wherein said step of providing a hearing aid housing includes providing a housing having a noncircular cross-section corresponding to said lumen cross-section.

10. The method of claim 1 further including providing a movable door for normally closing the open distal end of said shaft; and wherein
    said step of inserting said tool through said lumen to said distal end acts to open said door.

11. The method of claim 1 including the further step of inserting a tool into said ear canal for pushing said stud back into a desired position relative to said ear canal.

12. The method of claim 1 wherein said step of providing an elongate shaft includes providing visible depth markings on said shaft for facilitating said shaft distal end proximate to said patient's ear canal.

13. A medical device configured for implantation at a subcutaneous site in a patient's body comprising:
    a housing defining a body portion configured for mounting subcutaneously proximate to a patient's ear canal and a stud portion extending from said body portion for percutaneously projecting into said ear canal;
    an electroacoustic transducer mounted in said housing for projecting sound energy from said stud portion;
    said body portion defining a noncircular cross-section; and
    a porous layer carried by a peripheral surface area of said housing for promoting soft tissue ingrowth.

14. The device of claim 13 further including at least one anchor carried by said housing configured for movement from a retracted position to a deployed position for engaging soft body tissue.

15. In combination, a hearing aid housing and an instrument set for transporting said housing through a subcutaneous tunnel from a location behind a patient's pinna to a subcutaneous location proximate to the patient's ear canal, said combination comprising:
    said instrument set including an elongate shaft having a distal end configured for tunneling through soft body tissue to said subcutaneous location proximate to said ear canal, said shaft defining a lumen extending from an entrance opening to an exit opening at said distal end;

said hearing aid housing configured for passage through said entrance opening, said lumen, and said exit opening; and a pusher member configured for axial movement in said shaft for pushing said housing through said lumen for implanting at said subcutaneous location.

16. The combination of claim 15 wherein said lumen has a noncircular cross-section; and wherein said housing has a noncircular cross-section corresponding to said lumen cross-section.

17. The combination of claim 15 further including means for threadedly engaging said pusher member and said shaft for enabling said pusher member to be rotated to axially advance said housing toward said exit opening.

18. The device of claim 15 wherein said housing includes a body portion and a stud portion defining a longitudinally extending peripheral surface, and a shoulder between said body portion and said stud portion defining a laterally extending peripheral surface; and wherein a porous layer is formed on said longitudinally and/or laterally extending peripheral surfaces to promote tissue ingrowth.

19. The combination of claim 15 further including:

at least one anchor carried by said housing configured for movement between a retracted position and a deployed position; and wherein said anchor is held in said retracted position when said housing is in said lumen and is configured to automatically move to said deployed position when said housing is ejected from said shaft exit opening to engage subcutaneous tissue.

20. The combination of claim 15 wherein said instrument set further includes:

a hole forming tool having an elongate shank configured for removable insertion through said shaft lumen for forming a percutaneous hole opening into said patient's ear canal.

21. The combination of claim 20 wherein said elongate shank has a cutting edge at its distal end for cutting said percutaneous hole.

22. The combination of claim 21 wherein said shank is mounted for axial rotation to facilitate said cutting edge forming said percutaneous hole.

23. The combination of claim 21 further including means for selectively advancing said cutting edge beyond said shaft distal end for cutting said percutaneous hole.

24. The combination of claim 23 wherein said tool cutting edge defines a periphery for removing a plug of body tissue to form said percutaneous hole; and a rod movable relative to said cutting edge for removing any body tissue captured by said cutting edge.

25. The combination of claim 23 wherein said shank is hollow and said cutting edge defines a periphery for capturing a plug of body tissue to form said percutaneous hole; and a rod axially movable through said shank for ejecting said plug into said patient's ear canal.

26. The combination of claim 23 further including means for threadedly engaging said hole forming tool and said shaft whereby said tool can be axially rotated to incrementally advance said tool shank relative to said shaft.

27. The combination of claim 23 further including an anvil surface insertable into a patient's ear canal to allow said tool cutting edge to bear against said anvil surface to form said percutaneous hole.

28. The combination of claim 27 including a speculum having first and second jaws operable to spread said patient's ear canal to increase visibility; and wherein said anvil surface is formed on at least one of said jaws.

29. The combination of claim 21 wherein said hole forming tool and shaft are cooperatively configured to permit said tool to be axially rotated in a first mode to incrementally advance said tool shank relative to said shaft and in a second mode for freely spinning said shank in said shaft.

30. The combination of claim 15 wherein said shaft bears depth markings on its outer surface for indicating the magnitude of penetration of said shaft distal end.

31. The combination of claim 15 wherein said instrument set further includes:

an elongate obturator having a shank configured for removable insertion through said shaft lumen for closing said exit opening.

32. The combination of claim 15 further including a movable door mounted on said shaft for normally closing the open distal end of said lumen, said door being configured to be opened by a tool passed through said lumen.

* * * * *